United States Patent
Brightwell et al.

(10) Patent No.: US 6,395,902 B1
(45) Date of Patent: May 28, 2002

(54) OXATHIAZOLIDINYL PYRIDINES

(75) Inventors: Christopher Ian Brightwell; Robin Gerald Shepherd, both of Windsor (GB)

(73) Assignee: John Wyeth & Brother Limited, Maidenhead (GB)

( * ) Notice: Subject to any disclaimer, the term of this patent is extended or adjusted under 35 U.S.C. 154(b) by 0 days.

(21) Appl. No.: 09/614,792

(22) Filed: Jul. 12, 2000

Related U.S. Application Data

(62) Division of application No. 09/012,066, filed on Jan. 22, 1998, now Pat. No. 6,133,449, which is a division of application No. 09/010,741, filed on Jan. 16, 1998, now Pat. No. 6,175,012, which is a division of application No. 08/459,601, filed on Jun. 2, 1995, now abandoned.

(30) Foreign Application Priority Data

Jun. 3, 1994 (GB) .............................................. 9411108
May 19, 1995 (GB) .............................................. 9510152

(51) Int. Cl.$^7$ ........................................... C07D 419/04
(52) U.S. Cl. .................................................. 546/268.4
(58) Field of Search ....................... 546/268.4; 544/544

(56) References Cited

U.S. PATENT DOCUMENTS

| | | | |
|---|---|---|---|
| 4,652,633 A | 3/1987 | Lamm | 564/218 |
| 4,741,831 A | 5/1988 | Grimstead | 210/638 |
| 4,764,514 A | 8/1988 | Ueda | 514/252 |
| 5,271,812 A | 12/1993 | Gao | 204/59 R |
| 5,439,915 A * | 8/1995 | Commons et al. | 514/292 |
| 5,516,910 A | 5/1996 | Cooper | 546/114 |
| 5,519,027 A | 5/1996 | Schwede | 514/277 |
| 5,723,464 A * | 3/1998 | Brightwell et al. | 514/254 |
| 6,175,012 B1 * | 1/2001 | Brightwell et al. | 544/360 |

FOREIGN PATENT DOCUMENTS

| | | |
|---|---|---|
| EP | 0200024 | 4/1986 |
| EP | 0368169 | 11/1989 |
| EP | 0512755 | 4/1992 |
| WO | WO9502592 | 1/1995 |
| WO | WO95/02592 * | 1/1995 |

OTHER PUBLICATIONS

Yoshikawa et al, CA 71:81110b (1969).
Yoshikawa et al. CA 71:81293p (1969).
Grinstead, CA 109: 76111 (1988).
Mega et al., CA 114: 243866 (1999).
Ukachi et al., J. Opt. Soc. Am. B. Opt. Phys. 10, 1372–78 (1993).
Bornatsch et al., Chem. Berichte, 114, 937–945 (1981).
S. Tamura et al., Chem. Pharm. Bull., 26, 3167–77 (1978).

* cited by examiner

*Primary Examiner*—Jane Fan
(74) *Attorney, Agent, or Firm*—Rebecca R. Barrett

(57) ABSTRACT

Compounds having the formula $$R^5O-A-NR^4-R^2 \quad\quad (V)$$

where $R^2$ is a heteroaryl group linked to the remainder of the molecule via a carbon atom adjacent a nitrogen atom and $R^4$ and $R^5$ are both hydrogen atoms or together represent —SO— or —SO$_2$— and A is C$_2$–C$_4$ alkylene optionally substituted by one or more lower alkyl groups are novel intermediates in the preparation of pharmaceutically useful piperazine derivatives as end compounds. The compounds having formula V where $R^4$ and $R^5$ are hydrogen may be prepared by a rearrangement of a compound having the formula (VI).

$$R^2O-A-NH_2 \quad\quad (VI)$$

3 Claims, No Drawings

OXATHIAZOLIDINYL PYRIDINES

This is a divisional of U.S. Ser. No. 09/012,066 Jan 22, 1998 now U.S. Pat. No. 6,133,449, which is a div. of U.S. Ser. No. 09/010,741, filed Jan. 22, 1998, U.S. Pat. No. 6,175,012, issued Jan. 16, 2001, which is a divisional of U.S. Ser. No. 08/459,601, filed Jun. 2, 1995, now abandoned.

The present invention relates to a process for the preparation of N-[heteroaryl]hydroxyalkylamines, novel N-[heteroaryl]hydroxyamines obtainable by the process and processes for preparing piperazine derivatives using the N-[heteroaryl]hydroxyalkylamines.

GB 2 255 337A discloses piperazine derivatives having the general formula I

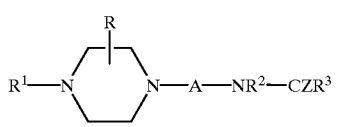

(I)

and their pharmaceutically acceptable acid addition salts as 5-HT$_{1A}$ binding agents, particularly 5-HT$_{1A}$ antagonists and, in particular, their use in the treatment of CNS disorders, for example, anxiolytics. They may also be used as antidepressants, hypertensives and as agents for regulating the sleep/wake cycle, feeding behaviour and/or sexual function.

In formula I above A is C$_{2-4}$ alkylene optionally substituted by one or more lower alkyl groups, Z is oxygen or sulphur, R is hydrogen or lower alkyl, R$^1$ is an optionally substituted monocyclic or bicyclic aryl or heteroaryl radical, R$^2$ represents an optionally substituted monocyclic or bicyclic heteroaryl and R$^3$ represents inter alia hydrogen, lower alkyl, cycloalkyl, cycloalkenyl, cycloalkyl (lower) alkyl, aryl, aryl (lower) alkyl and heteroaryl (lower) alkyl.

GB 2 255 337A also discloses piperazine derivatives having the general formula II (II)

R$^1$—N⟨ ⟩N—A—NHR$^2$ where R, R$^1$, R$^2$ and A are as defined above as chemical intermediates for the preparation of the piperazine derivatives having the general formula I. The chemical intermediates are reacted with an acid having the formula R$^3$—CZ—OH where R$^3$ and Z are as defined above or a reactive derivative of such an acid to prepare the compounds having formula I. The chemical intermediates were prepared by the following process:

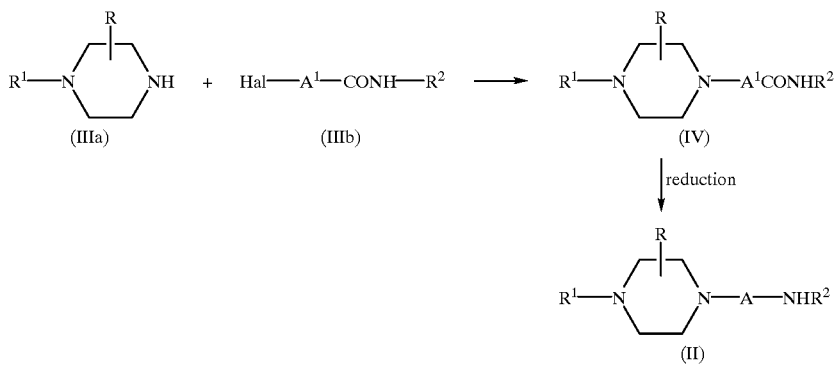

(where R, R$^1$, R$^2$ and A are as defined above, Hal is halo, particularly chloro or bromo and A' is an alkylene chain of 1 to 3 carbon atoms optionally substituted by one or more lower alkyl groups)

The reduction may be carried out with, for example, a boron reducing agent eg boranedimethyl sulphide or a complex metal hydride, e.g. lithium aluminium hydride.

The present invention is based upon the discovery that the aforesaid chemical intermediates having formula II can be prepared by means of a process involving a novel rearrangement reaction. The rearrangement reaction has the advantages that it can be performed in high yields and that it can be carried out as an asymmetric synthesis for the preparation of particular stereosomeric forms.

The present invention provides novel compounds having formula V $$R^5O—A—NR^4—R^2 \qquad (V)$$

and the salts thereof in which A is as defined above; R$^2$ represents a group having the formula R$^6$—N=CR$^7$— where R$^6$ and R$^7$, together with carbon atom and nitrogen atom to which they are attached, complete an optionally substituted monocyclic or bicyclic heteroaryl radical and R$^4$ and R$^5$ each represent a hydrogen atom or together represent —SO— or —SO$_2$—. Thus the compounds having formula V include the compounds having formula Va

HO—A—NH—R$^2$ (Va)

and compounds having formula Vb (Vb)

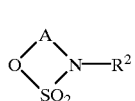

and compounds having the formula Vc

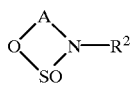
(Vc)

The term "heteroaryl" refers to an aromatic radical containing one or more hetero atoms (eg oxygen, nitrogen, sulphur) and which may be optionally substituted by one or more substituents. Examples of such substituents include lower alkyl (for example, methyl, ethyl and propyl), lower alkoxy (for example, methoxy and ethoxy), halogen, trifluoromethyl, nitro, cyano, di(lower alkyl)amino and (lower) alkoxycarbonyl. The heteroaryl radical may, for example, contain up to 10 ring atoms. Preferably the heteroaryl radical is a monocyclic radical containing 5 to 7 ring atoms. The hetero ring of $R^2$ must contain a nitrogen hetero atom and may also contain one or more further hetero atoms.

When $R^2$ is a bicyclic heteroaryl radical both rings of the radical may contain hetero ring atoms or only one ring may contain a hetero atom or atoms. In the latter instance the radical $R^2$ is connected to the rest of the molecule of formula (I) via the ring containing the hetero atom(s).

Examples of the heteroaryl radical $R^2$ include monocyclic radicals containing one hetero atom, eg optionally substituted 2-pyridyl, particularly 2-pyridyl, monocyclic radicals containing two hetero atoms, eg 2- or 4-thiazolyl (particularly 2-thiazoyl) and bicyclic radicals containing one or two hetero atoms eg 2-quinolinyl or 1- or 3-isoquinolinyl (particularly 2-quinolinyl).

The term "lower" as appplied to alkyl and alkoxy groups herein means that the alkyl or alkoxy group contains 1 to 6 carbon atoms preferably 1 to 4 carbon atoms. The term "(lower)" alkoxy carbonyl" means alkoxycarbonyl in which the alkoxy group is "lower". Examples of lower alkyl include methyl, ethyl, propyl, isopropyl, butyl, t-butyl, pentyl, isopentyl and hexyl.

The group A may represent dimethylene, trimethylene, tetramethylene or a lower alkyl-substitution product thereof, for instance, —CH(CH₃)—CH₂—. Where one or more lower alkyl substituents are present, the group A may contain an asymetric carbon atom. Thus the new compounds having formula V may exists in different steroisomeric forms. Different stereoisomers are preferably prepared by using a starting material of formula VII (see below) in a particular stereoisomeric form.

The invention provides a process for the preparation of a compound having formula Va HO—A—NH—$R^2$ (Va)

or a salt thereof where $R^2$ and A are as defined above, which comprises subjecting a compound having the formula VI $R^2$O—A—NH₂ (V)

where $R^2$ and A are as defined above, to rearrangement. The rearrangement can be carried out by heating the compound having formula VI in the presence of a suitable solvent, optionally in the presence of an acidic catalyst. The rearrangement reaction has the advantage that it can be carried out in very high yields.

The compounds having the formula VI can be prepared by ether formation in known manner from alcohols having the formula VII

HO—A—NH₂ (VII)

where A is as defined above. In particular the alcohol may be converted into an alkali metal salt thereof, particularly the sodium, potassium or lithium salt, in solution in a suitable solvent prior to reaction with a compound having the formula $R^2$—X where X is a leaving group, preferably, chloro, bromo or fluoro. The salt formation is preferably carried out by treating the alcohol (VII) with potassium t-butoxide in tetrahydrofuran to form the potassium salt of the alcohol.

The aminoalcohols having formula Va are useful for the preparation of alkylating agents for the introduction of a substituted alkyl group having the formula X

—A—NH—$R^2$ (X)

Such alkylating agents are reacted with a piperazine derivative having the formula IIIa

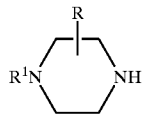
(IIIa)

where $R^1$ is as defined above to form the aforesaid chemical intermediates having formula II which in turn can be used to prepare the pharmaceutically useful piperazine derivatives having formula I.

We have found that conventional alkylating agents, namely, those of the formula RY where R is the alkyl or substituted alkyl group and Y is a leaving group such as a chlorine or bromine atom or tosyloxy group, are not generally suitable for use in the aforeside reaction with the piperazine derivative having formula IIa to prepare the compund having formula II. However, we have surprisingly found that the reaction is possible by using a compound having the formula Vb or Vc, preferably Vc as reactant. The compounds having the formulae Vb and Vc may be prepared by a process which comprises reacting a compound having the formula Va with a compund having the formula $SO_nX_2$ where n is 1 or 2 and X is a leaving group. X may be halogen particularly chlorine or a residue from imidazole. When n is 1 then the product of the process is of formula Vb. When n is 2 the product of the proces is of formula Vc. The compounds having formula Vc may also be prepared by oxidation of a compound having formula Vb. The oxidation may be carried out according to known methods.

The invention also includes a process for the preparation of a compound having the formula III or a salt thereof which comprises reaction of a compound having formula IIIa or a salt thereof with a compound having formula Vb or Vc, preferably a compound having formula Vc. The reaction may be followed by reaction with a compound having the formula HOCZ$R^3$ or a reactive dervative thereof in the preparation of compound of formula I or salt thereof.

The following reaction scheme illustrates a synthetic route according to the invention where Ar represents aryl, preferably substituted or unsubstituted phenyl, for example 2-methoxyphenyl:

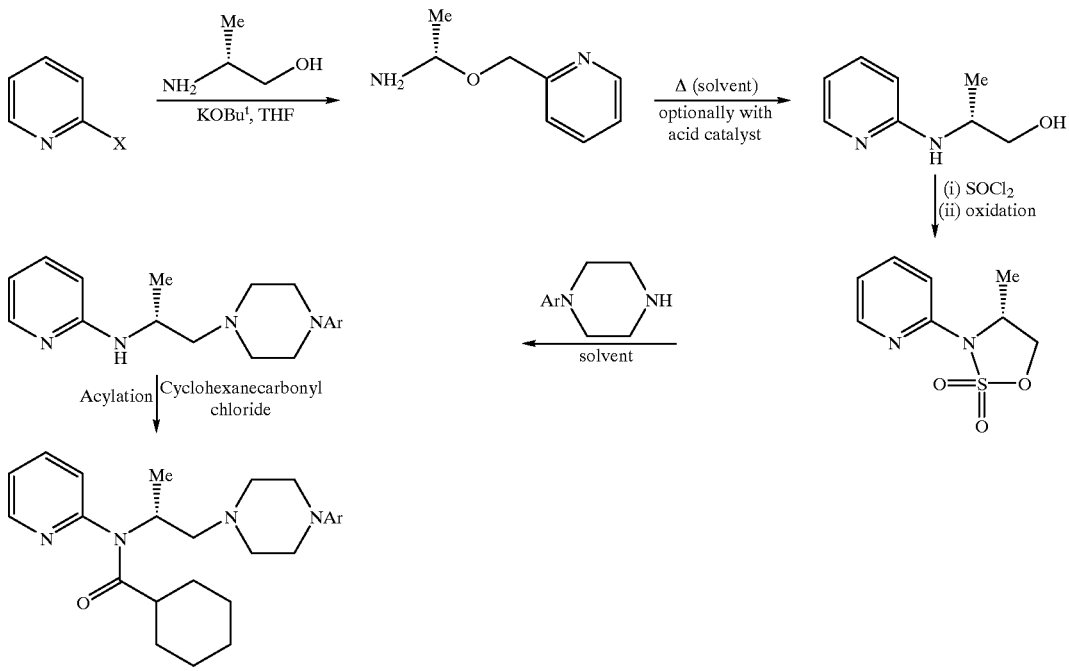

The chirality of the product of the reaction of the compound having formula Vb or Vc with the compound having formula IIIa at position 5 of the [1,2,3]oxathiazolidine ring is inverted during the reaction. The chirality at position 4 of the said ring is retained during the reaction.

The following Examples illustrate the invention:

EXAMPLE 1

(R)-4-Methyl -3-pyridin-2-yl[1,2,3]oxathiazolidine-2,2-dioxide (a) (R)-N-(2-Pyridyl)-2-aminopropanol (R)-Alaninol (107.3 g, 1.43M) was added dropwise with stirring to a solution of potassium tertiary butoxide (160 g, 1.43M) in tetrahydrofuran (1L). After the exothermic reaction had cooled to room termperature, 2-chloropyridine (162.4 g, 1.43M) was added dropwise. The reaction mixture was heated under reflux overnight, cooled, filtered and evaporated to an oil. The oil was dissolved in xylene (1,5L) and toluene-p-sulphonic acid (0.5 g) was added. The mixture was heated under reflux overnight. On cooling to room temperature the product crystallised to give (R)-N-(2-pyridyl)-2-aminopropanol (190 g), $[\alpha]_D^{26}=30°$ (c=1 in $CHCl_3$).

(b) (R)4-Methyl-3-pyrid-2-yl[1,2,3]-oxathiazolidine-2-oxide

A solution of (R)-N-(2-pyridyl)-2-aminopropanol (20.0 g, 0.13 moles) and N,N-diisopropylethylamine (33.6 g, 0.13 moles) in dichloromethane (500 ml) was cooled to 5° C. Then thionyl chloride (15.5 g, 0.13 moles) in dichloromethane (100 ml) was added slowly whilst the temperature was kept below 10° C. The mixture was stirred for 0.5 h. and ice cold water (500 ml) was added. The organic phase was separated and washed with water (5×500 ml). The aqueous phase was back-extracted with dichloromethane (2×500 ml), the organic phases were combined, dried ($MgSO_4$) and evaporated in vacuo to give a brown oil. This was purified on a silica column, eluting with diethyl ether to give (R)4-methyl-3-(2-pyridyl)-[1,2,3]oxathiazolidine 2-oxide (15.4 g) as a clear oil.

(c) (R)-4-Methyl-3-(2-pyridyl)-[1,2,3]-oxathiazolidine-2,2-dioxide

A solution of sodium periodate (21 g, 0.10 moles) in water (150 ml) was added slowly to a solution of (R)-4methyl-3-pyridin-2-yl-[1,2,3]oxathiazolidine-2-oxide (15.4 g, 0.78 moles) and ruthenium(III)chloride (20 mg) in acetonitrile (1540 ml) whilst the temperature was kept below 5° C. A heavy precipitate developed. The mixture was poured into a mixture of ethyl acetate (500 ml) and water (500 ml) and then shaken. The organic phase was retained and the aqueous phase was extracted with further ethyl acetate (2×500 ml). The organic phases were combined, backwashed with water (500 ml), dried ($MgSO_4$) and then evaporated in vacuo to give (R)-4-methyl-3-(2-pyridyl)-[1,2,3]-oxathiazolidine-2,2-dioxide (15.5 g) as a yellow oil.

EXAMPLE 2

(R)-1-(2-Methoxyphenyl)-4-[2-(methyl)-2-(2-pyridinylamino)ethyl]piperazine 12.02 grams of 1-(2-methoxyphenyl)piperazine and 13.4 grams of (R)-4-methyl-3-pyridin-2-yl[1,2,3] oxathiazolidine-2,2-dioxide were stirred together in 50 milliliters of acetonitrile at room temperature overnight. The solvent was removed in vacuo. The residue was heated in 100 milliliters of dilute hydrochloric acid for 30 minutes. The mixture was cooled, washed with dichloromethane, basified by using dilute sodium hydroxide solution and extracted by means of dichloromethane. The organic phase was washed with water, dried and evaporated to dryness to give 15.8 g of the title compound as a slightly crude product. The product was 85 to 95% pure and contained 2 main impurities derived from the sulphone. The crude product was used directly, i.e. without purification, by acylation by means of cyclohexanecarbonyl chloride to yield (R)-N-[1-methyl-2-[4-(2-methoxyphenyl)-1-piperazinyl]ethyl]-N-(2-pyridinyl) cyclohexanecarboxamide.

EXAMPLE 3

(R)-1-(2-Methoxyphenyl)-4-[2-(methyl)-2-(2-pyridinylamino)ethyl]piperazine 9.16 grams (46.6 millimoles) of 1-(2-methoxyphenyl) piperazine in one portion was added under argon to a solution of 10 grams (46.6 millimoles) of (R)-4-methyl-3-pyridin-2-yl[1,2,3]oxathiazolidine-2,2-dioxide in 200 milliliters of acetonitrile. The mixture became yellow. After ½ hour, the reaction mixture was heated to 50° C. for 1 hour and then stirred at room temperature overnight Then dilute hydrochloric acid was added. The mixture was washed with ethyl acetate, basified to pH 12 and extracted twice with ethyl acetate. The organic phases were washed with brine, dried (Mg SO$_4$) and subjected to evaporation to give 12.053 grams of the title compound which was purified by columning in the system ethyl ether/hexane (1:1) Al$_2$O$_3$ to afford 9.96 grams of the title compound.

EXAMPLE 4

(S)-Dihydro-5-methyl-3-(2-pyridyl)-3H-[1,2,3]oxathiadiazole-2,2-dioxide (a) (S)-N-(2-Pyridyl)-1-amino-2-propanol (S)-1-amino-2-propanol (43 g, 0.57M) was added to a stirred solution of potassium tertiary butoxide (64.2 g, 0.66M) in tetrahydrofuran (500 ml). 2-Chloropyridine (65.1 g 0.66M) was then added dropwise. After the exothermic reaction had subsided, the reaction was heated under reflux overnight, filtered to remove the potassium chloride and evaporated to an oil. The crude oil was dissolved in xylene (500 ml) and toluene-p-sulphonic acid (2 g) added and heated overnight under reflux under argon. After cooling to room temperature, the mixture was extracted with 2M hydrochloric acid. The acid extracts were basified with 2M sodium hydroxide and extracted into ethyl acetate. The ethyl acetate extracts were dried (MgSO$_4$) and after removal of the acetic acid the product was distilled affording 73.5 g of the title compound, bp 100–110° C. at 0.2 mbar.

(b) (5S)-4,5-Dihydro-5-methyl-3-(2-pyridyl)-3H-[1,2,3]oxathiazole-2-oxide

Thionyl chloride (8.8 ml, 14.35 g 0.12M) in dichloromethane (20 ml) was added dropwise to a cooled stirred solution of (S)-N-(2-pyridinyl)-1-amino-2-propanol (18.28 g, 0.12M) in dichloromethane (180 ml) and diisopropylethylamine (31 g, 0.24M) keeping the temperature below 5° C. After stirring at 0° for 1 h a solution of saturated sodium bicarbonate solution was added keeping the temperature below 5° C. The organic layer was separated, dried (Na$_2$SO$_4$) and concentrated to give 27.6 g of a yellow oil. The oil was chromatographed on silica using 40% ethyl acetate in hexane to give 20.28 g of a yellow oil containing a 4:3 mixture of diastereoisomers.

(c) (S)-4,5-Dihydro-5-methyl-3-(2-pyridyl)-3H-[1,2,3]oxathiazole-2,2-dioxide

A solution of sodium periodate (27.3 g 0.13M) in water (200 ml) was added with stirring to (S)-4,5-dihydro-5-methyl-3-(2-pyridinyl)-3H-[1,2,3]oxathiadiazole-2-oxide (20.23 g, 0.1M) in acetonitrile containing ruthenium III chloride (21 mg, 0.1 mmole, 0.1 mole %) at −10° C. over a period of 25 minutes. After stirring at 0° for 1 h, at room temperature for 2 h, the reaction mixture was added to water (800 ml) and extracted with ethylacetate (2×200 ml) dried (Na$_2$SO$_4$) and evaporated to an oil under reduced pressure (temperature <30° C.). Trituration with acetonitrile gave an off-white solid, 14.86 g, mp 99–100° C. (decomp) $[\alpha]_D^{27}$+28° [c=1 in CHCl$_3$). Found: C,44.9; H,4.65; N,13.0% C$_8$H$_{10}$N$_2$O$_3$S requires C, 44.85; H, 4.7; N, 13.1%.

EXAMPLE 5

(a) (R)-1-(2-Pyridyl)-4-ethyloxathiazolidine-2-oxide

Thionyl chloride (10 ml, 0.13 mol) in dichloromethane was added dropwise to a mixture of (R)-2-(2-pyridylamino)-1-butanol (20 g, 13 mol) and diisopropylamine (45 ml, 2 eq) in dichloromethane (500 ml) at −10° C. The temperature was kept below −5° C. during the addition. Stirring at −10° C. for 30 minutes was followed by the addition of cold water (500 ml). The mixture was basified using K$_2$CO$_3$, then the organic layer was separated and the aqueous layer extracted by dichloromethane (500 ml). The combined organic phases were washed with water and brine, dried and evaporated to dryness. The yellow oil was filtered through a pad of silica with ether as eluent to give the title compound. It exists as a mixture of isomers. $[\alpha]_D^{26}$ (c=1,CHCl$_3$) is −8° for one isomer and −339° for the other isomer.

The R-2-(2-pyridylamino)-1-butanol was prepared in a similar manner to Example 1(a) using (R)-2-amino butanol instead of (R)-2-aminopropanol. The (R)-2-(2-pyridylamino)-1-butanol exhibited the following NMR data in chloroform at 200 MHz: 8.00 (dd,1p), 7.38(dt,1p), 6.55 (dt,1p), 6.45(dd,1p), 4.55(d,br), 3.5 to 3.8 (m,4p), 1.5 to 1.7 (m,2p) and 1.97 (t,3p).

(b) (4R)-1-(2-Pyridyl)-4-ethyloxathiazolidine-2,2-dioxide

A solution of sodium periodate (21 g, 120 mmol) in water (150 ml) was added dropwise to a cooled (−10° C.) mixture of the sulphoxide (15 g) and ruthenium III chloride (20 mg) as catalyst over 1 hour, keeping the temperature below −5° C. A precipitate was formed during the addition. The mixture was warmed to room temperature and stirred for 1 hour until it showed no remaining starting material. Pouring into ethyl acetate (500 ml) and water (500 ml) was followed by extraction of the aqueous with ethyl acetate. The combined organic phases were washed with water (2×500 ml) and brine (500 ml), dried and evaporated to dryness to give the title compound,. $[\alpha]_D^{27}$=−51° (c=1, CHCl$_3$).

(c) (R)-1-(4-Indolyl)-4-[2-ethyl-2-(2pyridylamino)ethyl]piperazine)

4-Piperazinoindole, whose preparation is described in Example 7(a), (3.0 g, 14,9 mmol) and the compound obtained in part (b) (3.4 g, 1 eq) were stirred in acetonitrile for 1 hour. String was then continued until the reaction was shown to be complete by tic. The mixture was hydrolysed by the addition of dilute hydrochloric acid. The aqueous layer was separated, washed with water and brine, dried and evaporated to dryness. The crude product was purified by column chromatography (SiO$_2$, MeOH:DCM, 5:95) giving a grey oil. A portion (0.75 g) was dissolved in dichloromethane and converted to the hydrochloride salt with ethanolic hydrogen chloride. Solvent was removed in vacuo and the white solid recrystallised from isopropyl alcohol to give an amine dihydrochloride, $[\alpha]_D^{27}$=−32° (c=0.7, MeOH).

(d) (R)-N-(1-Ethyl-2-(4-indolyl-1-piperazinylethyl)-N-(2-pyridyl)cyclohexane carboxamide Cyclohexanecarbonyl chloride (0.6 ml) was added to a mixture of the amine (1.4 g) and triethylamine (0.8 ml) in dichloromethane (50 ml). The mixture was evaporated to dryness and partitioned between dilute hydrochloric acid and dichioromethane. The aqueous phase was basified and extracted by dichloromethane, washed with water and brine, dried over MgSO$_4$ and evaporated to dryness. The resulting mixture (product and triethylamine) was triturated with hexane, affording the amide as a white solid. The dihydrochloride was made by reaction with hydrogen chloride in isopropyl alcohol. The salt had a melting point of 133–135° C. and an optical rotation $[\alpha]_D^{27}$−52° (c=1,MeOH).

EXAMPLE 6

(a) (4R)-1-(2-Pyridyl)-4-methyloxathiazolidine-2-oxide

Thionyl chloride (0.11 moles) was dissolved in dichloromethane (100 ml). The solution was then added slowly to a stirred solution of imidazole (27.2 g 0.40 moles) in dichloromethane (300 ml) over one hour. A precipitate developed. Next, R-N-(2-pyridyl)-2-aminopropanol (15.2 g 0.10 moles) in dichloromethane (200 ml) was added slowly, keeping the temperature about 5° C. The reaction was exothermic after the addition was complete (1 hour), the reaction mixture was washed with water (3×500 ml), dried (MgSo$_4$) then evaporated in vacuo to give a yellow oil which was the sulphoxide (18.7 g).

(b) (R)-1-(4-Indolyl)-4-[2-methyl-2-(2-pyridylamino)ethyl piperazine])

4-Piperazinoindole (7.7 g) and the sulphoxide as prepared in part (a) (7.5 g) were dissolved in anhydrous tetrahydrothiophene-1,1-dioxide (100 ml), then heated under argon at 80° C. for 24 hours. Additional piperazinyl indole (0.5 g) was added, then the mixture was poured into butyl methyl ether (500 ml), washed with water (3×500 ml), then evaporated in vacuo to give a brown foamy/glassy oil (7.2 g) which was shown by NMR to comprise the title compound at about 90% purity.

EXAMPLE 7

(R)-N-(1-Methyl-2-(4-indolyl-1-piperazinylethyl)-N-(2-pyridyl)cyclohexanecarboxamide (a) 4-Piperazinoindole 4-Aminoindole hydrochloride (89.4 g, 0.53 mole) bis-chloroethylamine HCl (94.5 g. 0.53 mole) and disopropyl-ethylamine (185 ml, 1.03 mole) were stirred and heated under reflux in chlorobenzene (1L) under argon for 3 h. Diisopropylethylamine (92.5 ml, 68.5 g, 0.5 mole) was then added slowly over 1 h. The mixture was heated under reflux for a further 1 h and left at room temperature over night. The resulting gum was dissolved in isopropanol (500 ml). After evaporation to dryness the product was re-evaporated with toluene to leave a black gum. After tritration with a mixture of ethyl acetatelisopropanol the solid was filtered and washed with methanol affording 90 g of crude 4-piperazinoindole hydrochloride as a slate grey powder.

The grey powder was dissolved in water (1L), made basic with sodium hydroxide solution then extracted with dichloromethanelmethanol (3L of CH$_2$Cl2:MeOH 10:1). After the organic layer was washed with water, it was dried (MgSO$_4$) and evaporated under reduced pressure to leave a grey solid. The solid was triturated with isopropanol/ethylacetate and filtered to give 40 g of a pale grey solid.

(b) (R)-1-(4-Indolyl)-4-[2-methyl-2-(2-pyridylamino)ethyl] piperazine

A solution of (R)-4-methyl-3-pyridin-2-yl-[1,2,3]-oxathiazolidine-2,2-dioxide (4.04 g 0.019 moles) prepared according to Example 1 and 4-piperazinoindole (3.80 g 0.019 moles) in acetonitrile (200 ml) was heated to 60° C. for 0.5 h then evaporated in vacuo. The residue was taken up into dilute hydrochloric acid (100 ml), warmed to 60° C. for 0.5 h, cooled, washed with ethyl acetate (2×100 ml), made basic with potassium carbonate, extracted into dichloromethane (3×100 ml), dried (MgSO$_4$) then evaporated in vacuo to give a brown glass. This was purified on a silica column eluting with 10% propan-2-ol in dichloromethane to give (R)-1-(4-indolyl)-4-[2-methyl-2-(2-pyridylamino) ethyl]piperazine (4.3 g) as a clear glass.

(c) (R)-N-(1-Methyl-2-(4-indolyl-1-piperazinylethyl)-N-(2-pyridyl)cyclohexanecarboxamide A solution of (R)-1-(4-indolyl)-4-[2-methyl-2-(2-pyridylamino)ethyl piperazine (4.3 g 0.012 moles), triethylamine (2.47 g 0.024 moles) and cyclohexanecarbonyl chloride (1.8 g 0.012 moles) in dichloromethane (100 ml) was warmed to 60° C. for 0.5 h then evaporated in vacuo. The residue was taken up into dilute HCl (100 ml), washed with ethyl acetate (3×100 ml) made basic with potassium carbonate, extracted into dichloromethane (3×100 ml), backwashed with water (100 ml), dried (MgSO$_4$), then evaporated in vacuo to give (R)-N-(1-methyl-(4-indolyl-1-piperazinyl)ethyl-N-(2-pyridyl)cyclohexane carboxamide (4.3 g 80%) as a pale pink crystalline solid. The product was dissolved in methanol then treated with one mole equivalent of dilute hydrochloric acid. After evaporation to dryness and re-evaporation with isopropanol the product crystallised from IPA/Et$_2$O as the monohydrochloride, white microcrystals mp 154–156.5° C. Found: C:67.0; H:7.6; N14.4% C$_{27}$H$_{35}$N$_5$O.HCl requires: C:67.3; H:7.5; N: 14.7%.

EXAMPLE 8

(R)-N-(2-Methyl-(4-indolyl-1-piperazinyl)ethyl-N-2-(pyridyl)cyclohexanecarboxamide (a) (R)-1-(4-Indoly)-4-[2-methyl-2-(2-pyridylaminoethyl) piperazine A mixture of (S)-4,5-dihydro-5-methyl-3-(2-pyridinyl)-3H(1,2,3)oxathiazole-2,2-dioxide (2.02 g, 9.5 mM), prepared according to Example 4, 4-piperazinoindole (1.9 g, 9.5 mM) in acetonitrile (100 ml) was stirred and heated for 1 h. The solvent was removed under reduced pressure and the residue dissolved in dilute hydrochloric acid. The solution was heated to 60° C. for 10 minutes and then washed with CH$_2$Cl$_2$ (100 ml). The solution was basified (K$_2$CO$_3$) and extracted with dichloromethane (2×100 ml) containing some methanol. The remaining solid was filtered, the organic fraction washed with water, dried (MgSO$_4$) and evaporated to a dark brown material 2.5 g. The oil was dissolved in methanol and treated with a solution of hydrogen chloride in dry ether affording a white precipitate of the hydrochloride mp 125–130° C., $[\alpha]_D^{24}$ –16° [c=1 in MeOH]. Found: C, 53.9; H, 6.75; N, 15.5%. C$_{20}$H$_{25}$NS 2HCl.2H$_2$O requires C, 54.0; H, 7.0; N, 15.8%.

(b) (R)-N-(2-Methyl-(4-indolyl-1-piperazinyl)ethyl-N-(2-pyridyl)cyclohexane carboxamide Cyclohexane carboxylic acid chloride (0.53 g, 3.6 mM) in dichloromethane (20 ml) was added dropwise to a stirred solution of the amine obtained in Example 2(d) (1.26 g, 3.6 mM) and triethylamine in dichloromethane (20 ml). After heating to 50° for 20 m, and removal of the solvent, the residue was taken up in dilute hydrochloric acid. After filtering the solution was basified (K$_2$CO$_3$) and extracted with dichloromethane. After drying (MgSO$_4$) the solvent was removed to give a brown glass which was dissolved in ethylacetate and a solution of hydrogen chloride in dry ether added affording 1.5 g of the title compound as the hydrochloride, mp 125–130° as a white powder, $[\alpha]_D^{24}$ +25° [c=1 in MeOH]. Found: C, 63.6; H, 7.4; N, 13.6. C$_{27}$H$_{35}$N$_5$O 1.5HCl.0.5H$_2$O requires C, 63.7; N, 7.4; N, 13.8%.

EXAMPLE 9

(R)-1-(4-Indolyl)4-[1-ethyl-2-(2-pyridinylamino) ethyl]piperazine (a) (S)-1-(2-Pyridylamino)butan-2-ol (S)-1-Aminobutan-2-ol (35 millimoles), potassium tertiary butoxide (77 millimoles) and 2-chloropyridine (38.5 millimoles) were used in a similar manner to Example 1(a) to obtain the title compound, $[\alpha]_D^{26}$=+10° (1.12% concentration in trichloromethane).

(b) 4.5-Dihydro-5(S)-ethyl-3-(2-pyridyl)-3H[1,2,3] oxathiazole-2-oxide

Thionyl chloride (18.98 millimoles) in dichloromethane (20 ml) is added dropwise to imidazole (4.7 g, 69 millimoles) in dichloromethane (50 ml) under argon. Then after 15 minutes the title compound of part (a) (17.26 millimoles) in 25 ml of dichloromethane was added slowly at a temperature maintained below 5° C. After an hour at a temperature range of 0° to 5° the temperature was allowed to warm up to room temperature. After 1 hour, water was added The organic layer was separated and the aqueous layer was subjected to extraction with dichloromethane. The combined organic portions were washed twice with water, dried (sodium sulphate) and evaporated to give the title compound as an orange oil (3.325 g, 15.66 millimoles), NMR data δ (400 MHz; CDCl$_3$) 1.11 (1.5H, t, J 8 Hz), 1.12 (1.5H, t, J 8 Hz), 1.88–2.05 (1.5H, m), 2.11–2.22 (0.5H, m), 3.32 (0.5H, dd, J 10 and 8 Hz), 3.74 (0.5H, dd, J 10 and 7 Hz), 3.93–4.02 (1H, m), 4.84–4.91 (0.5H, m), 5.35–5.42 (0.5H, m), 6.63 (0.5H, d, J 8Hz), 6.73 (0.5H, d, J 8 Hz), 6.88–6.94 (1H, m), 7.59–7.65 (1H, m) and 8.25–8.30 (1H, m).

(c) 4,5-Dihydro-5(S)-ethyl-3-(2-pyridinyl)-3H[1,2,3] oxathiazole-2,2-dioxide

Ruthenium trichloride (25 mg) was added to water/ethyl acetate (16 ml of each) cooled to 10° C. To this there were then simultaneously and slowly added (1) a solution of the title compound of part (b) (3.257 grams, 15.35 millimoles) in 16 ml of ethyl acetate and (2) a bleach solution [12.8 ml of aqueous sodium hypochlorite (14% concentration)]. A further 10 ml of the bleach solution was added. The mixture was stirred for 30 minutes, then the organic layer was separated. The aqueous layer was subjected to extraction three times with ethyl acetate. Then the combined organic portions were washed twice with water, once with dilute hydrochloric acid, twice again with water, dried (sodium sulphate) and evaporated to give the title compound as an off-white solid (3.239 g, 14.2 millimoles), $[\alpha]_D^{27}$=+31° (0.99% concentration in trichloromethane).

(d) R-1-(4-Indolyl)-4-[1-ethyl-2-(2-pyridinylamino)ethyl) piperazine

The product of part (c) (3.105 g, 13.60 millimoles) and finely powdered 4-piperazinoindole were heated together in 100 ml acetonitrile under argon. After 2 hours the mixture was subjected to evaporation and methanol was added to the residue. The product was acidified with about 20 ml dilute hydrochloric acid. The mixture was stirred for 20 minutes, then evaporated. The residue was partitioned between dichloromethane and 1N sodium hydroxide. The aqueous phase was treated with dichloromethane. The organic phases were combined and washed with water, dried (sodium sulphate) and evaporated to give an oily residue which was treated on a column (diethyl ether, hexane and alumina) to afford 2.256 g of the title compound, $[\alpha]_D^{26}$=−20° (1.22% concentration in trichloromethane).

The novel compounds having formula V provided by this invention can also be used to prepare compounds described and claimed in our British patent application No. 9411099.6 filed Jun. 3, 1994 entitled "PIPERAZINE DERIVATIVES" (Our Case H-452).

What is claimed is:

1. A compound having formula V

$$R^5O\text{—}A\text{—}NR^4\text{—}R^2 \qquad (V)$$

or a salt thereof in which A is $C_{2-4}$ alkylene optionally substituted by one or more alkyl groups; $R^2$ represents a group having the formula $R^6$—N=CR$^7$— where $R^6$ and $R^7$, together with carbon atom and nitrogen atom to which they are attached form a pyridyl group and $R^4$ and $R^5$ together represent —SO— or —SO$_2$—.

2. A compound as claimed in claim 1, wherein A contains an asymmetric carbon atom, the compound being in a particular stereoisomeric form.

3. A compound selected from (5S)-4,5-dihydro-5-methyl-3-(2-pyridyl)-3H-[1,2,3] oxathiazole-2-oxide, and (5S)-4,5-dihydro-5-methyl-3-(2-pyridyl)-3H-[1,2,3] oxathiazole-2,2-dioxide.

* * * * *